United States Patent
Engel et al.

(10) Patent No.: US 9,113,796 B2
(45) Date of Patent: Aug. 25, 2015

(54) METHOD AND DEVICE FOR ADJUSTING THE VISUALIZATION OF VOLUME DATA OF AN OBJECT

(75) Inventors: Klaus Engel, Nürnberg (DE); Anna Jerebko, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 458 days.

(21) Appl. No.: 13/487,227

(22) Filed: Jun. 3, 2012

(65) Prior Publication Data

US 2012/0308095 A1 Dec. 6, 2012

(30) Foreign Application Priority Data

Jun. 3, 2011 (DE) .................. 10 2011 076 930

(51) Int. Cl.
  G06K 9/00 (2006.01)
  A61B 6/02 (2006.01)
  G06T 15/08 (2011.01)
  A61B 6/03 (2006.01)
  A61B 6/00 (2006.01)
  A61B 8/08 (2006.01)
  A61B 8/13 (2006.01)
  A61B 8/00 (2006.01)

(52) U.S. Cl.
  CPC .............. *A61B 6/025* (2013.01); *A61B 6/463* (2013.01); *A61B 6/466* (2013.01); *A61B 6/502* (2013.01); *A61B 6/5223* (2013.01); *G06T 15/08* (2013.01); *A61B 6/03* (2013.01); *A61B 6/037* (2013.01); *A61B 6/4441* (2013.01); *A61B 6/469* (2013.01); *A61B 6/5217* (2013.01); *A61B 8/0825* (2013.01); *A61B 8/13* (2013.01); *A61B 8/463* (2013.01)

(58) Field of Classification Search
  None
  See application file for complete search history.

(56) References Cited

U.S. PATENT DOCUMENTS

| | | | |
|---|---|---|---|
| 6,016,439 A * | 1/2000 | Acker | 600/411 |
| 6,608,628 B1 * | 8/2003 | Ross et al. | 345/619 |
| 7,085,406 B2 * | 8/2006 | Alyassin | 382/131 |
| 7,760,924 B2 | 7/2010 | Ruth et al. | |
| 7,868,900 B2 * | 1/2011 | Sirohey et al. | 345/592 |
| 7,889,194 B2 * | 2/2011 | Engel et al. | 345/419 |
| 8,165,365 B2 * | 4/2012 | Bernard et al. | 382/128 |
| 8,581,902 B2 * | 11/2013 | Zegdoun et al. | 345/420 |
| 8,641,621 B2 * | 2/2014 | Razzaque et al. | 600/437 |
| 2004/0070584 A1 * | 4/2004 | Pyo et al. | 345/419 |
| 2005/0074155 A1 * | 4/2005 | Alyassin | 382/131 |
| 2006/0245536 A1 * | 11/2006 | Boing et al. | 378/8 |
| 2007/0195088 A1 * | 8/2007 | Engel et al. | 345/424 |
| 2007/0229500 A1 * | 10/2007 | Engel et al. | 345/422 |
| 2007/0279435 A1 * | 12/2007 | Ng et al. | 345/624 |
| 2009/0028398 A1 | 1/2009 | Lundstrom | |

(Continued)

OTHER PUBLICATIONS

German Office Action dated Apr. 5, 2012 for corresponding German Patent Application No. DE 10 2011 076 930.7 with English translation.

*Primary Examiner* — Wenpeng Chen
(74) *Attorney, Agent, or Firm* — Lempia Summerfield Katz LLC (57) ABSTRACT

An adjustment of the visualization of volume data of an object as an image with regard to diagnostically relevant medical information relating to the environment of a region under investigation is provided. In the process, at least one slice region is specified in accordance with slice information within the volume data. A first mapping of a value range of the volume data is used for visualizing the at least one slice region on a display. A second mapping different from the first mapping is used for visualizing a region bordering on the at least one slice region on the display.

15 Claims, 7 Drawing Sheets

(56) References Cited

U.S. PATENT DOCUMENTS

| | | | |
|---|---|---|---|
| 2009/0034684 A1* | 2/2009 | Bernard et al. | 378/98 |
| 2009/0080752 A1 | 3/2009 | Ruth et al. | |
| 2009/0087045 A1* | 4/2009 | Partain et al. | 382/128 |
| 2009/0123052 A1 | 5/2009 | Ruth et al. | |
| 2009/0187385 A1* | 7/2009 | Zegdoun et al. | 703/1 |
| 2010/0104160 A1 | 4/2010 | Lavi et al. | |
| 2010/0142788 A1* | 6/2010 | Matsumoto | 382/131 |
| 2010/0166267 A1 | 7/2010 | Zhang et al. | |
| 2010/0226552 A1* | 9/2010 | Ekin | 382/131 |
| 2010/0324422 A1* | 12/2010 | Wanda et al. | 600/443 |
| 2011/0137156 A1* | 6/2011 | Razzaque et al. | 600/424 |
| 2013/0034282 A1* | 2/2013 | Kaufman et al. | 382/128 |

\* cited by examiner

METHOD AND DEVICE FOR ADJUSTING THE VISUALIZATION OF VOLUME DATA OF AN OBJECT

This application claims the benefit of DE 10 2011 076 930.7, filed on Jun. 3, 2011.

BACKGROUND

The present embodiments relate to a method, a device and a computer program for adjusting the visualization of volume data of an object as an image.

The use of X-rays in medical diagnosis is a widely established practice. Thus, for example, the examination of female breast tissue for the formation of carcinomas may be carried out using X-ray radiation (e.g., mammography).

Owing to the specific anatomical features of the region of the body being examined, special-purpose devices, which may be referred to as mammography devices, are used for examinations of the type using X-rays.

Projection settings of mammography devices have become established as standard settings for diagnostic purposes. The following two standard settings may be used.

The mediolateral oblique (MLO) view of the breast (e.g., oblique projection) is the standard setting employed in the early detection of breast cancer by mammography. An image of the breast is recorded at a 45° angle. The 45° oblique projection is intended to image the upper outer quadrants, the axillary tails and the inframammary folds.

Alongside this, there is also the craniocaudal (CC) view, in which an image of the breast is recorded vertically from above. The CC projection may show as much breast tissue as possible and ideally images all breast sections except for the sections in the furthest lateral and axillary positions.

A procedure known as 2-plane mammography, which combines the mediolateral oblique (MLO) view and the craniocaudal (CC) view, may be carried out within the course of a standard examination.

Despite this combination of projections taken from different angles, conventional mammography has its limits. There is the risk that tissue hardening (e.g., calcifications) is concealed in the X-ray image by other structures and is not diagnosed.

Tomosynthesis, which is employed, for example, in digital mammography, provides improved diagnostic possibilities. In contrast to computed tomography, tomosynthesis is based on only one comparatively small angular interval being scanned in the course of the movement of the X-ray tube around the object that is to be examined. The restriction of the interval may be determined by the examination object (e.g., female breast).

A sequence of tomosynthesis projections in mammography may be acquired by a modified mammography system or a breast tomosynthesis system. In this case, for example, 25 projections are taken while the X-ray tube moves over the detector in an angular range between −25° and 25°. The radiation is triggered at regular intervals during this movement, and one projection is read out from the detector each time. A three-dimensional representation of the examined object is subsequently reconstructed in the computer from the projections in a tomosynthesis reconstruction process. The object may be present in the form of grayscale values that constitute a metric for the density at voxels or points in space associated with the grayscale values. The Z layers of the reconstructed volume (e.g., reconstructed slice images that are aligned parallel to the detector plane) are examined in most cases in the course of the medical diagnosis.

An improvement in the examination of Z layers may be achieved using visualization techniques for three-dimensional volume datasets.

Techniques collectively known as volume rendering are employed in order to represent three-dimensional volumes as an image on a monitor. One example of such a technique (e.g., direct volume rendering) is ray casting (e.g., the simulation of rays penetrating the volume). Another technique is, for example, multiplanar reformation (e.g., multiplanar reconstruction (MPR)). This is a two-dimensional image reconstruction method, in which raw data present as transversal slices is used to compute frontal, sagittal, oblique or curved slices that assist the viewer in the anatomical orientation. In the maximum intensity protection (MIP) method, the point having the maximum grayscale value from the 3D volume along the observational axis is imaged directly in each case. A two-dimensional projection image is generated. A spatial context is created in this way when a series of MIP images is viewed from different observer positions. This method may be used for visualizing structures filled with contrast agent.

The application of methods of this type for visualizing tomosynthesis data is described, for example, in the publications US 20100166267 A1, US 20090034684 A1, U.S. Pat. No. 7,760,924 and US 20090080752 A1.

With all these methods, it is taken into account that a large bandwidth of different density (and hence a further range of grayscale values) occurs in the volume data that may be present in the form of grayscale values. A scale named for the scientist Hounsfield and extending approximately from −1000 (e.g., for lung tissue) to 3000 (e.g., for bone) may be used to describe the reconstructed attenuation values. A grayscale level is assigned to every value on this scale, resulting in a total of approximately 4000 grayscale levels to be visualized. This scheme, which is customary in CT for three-dimensional image constructions, may not simply be transferred to monitors used for visualization purposes. One reason for this is that no more than 256 (e.g., $2^8$) grayscale levels may be visualized on a commercially available 8-bit monitor. There is little point in representing a higher number of grayscale levels because the imaging granularity of the display already significantly exceeds that of the human eye, which may distinguish approximately 35 grayscale levels. Efforts are therefore directed at extracting the diagnostically relevant details for the purpose of visualizing human tissue. One possibility for this is the definition of windows encompassing a particular grayscale value range at a level that is relevant for the diagnosis. A term also employed in this context is "window leveling." Histologically calcified lesions, for example, may have grayscale values in the range of approximately 500 Hounsfield units. In order to diagnose such calcifications (e.g., in mammography), a window may be set in a range around 500 Hounsfield units. With this approach or, more specifically, this window, the adipose and connective tissue of the breast, which lies in the negative Hounsfield unit range, may disappear. A similar situation arises in the case of volume rendering, in which the relevant structures are made visible by transfer functions that map grayscale values to color values and permeability coefficients (e.g., opacity values). With that technique, the adipose and connective tissue may be rendered as transparent so that calcifications may be seen.

With this approach, it is taken into account that the diagnosis of malignant changes is a complex undertaking. Thus, larger calcifications may be benign, while smaller calcifications (e.g., microcalcifications) are indicators of a tumor formation. In order to arrive at a better assessment, the physician requires as much relevant information as possible about the region of the tissue transformation and the embedding of the changed tissue in the surrounding tissue layers.

SUMMARY AND DESCRIPTION

The present embodiments may obviate one or more of the drawbacks or limitations in the related art. For example, the visualization of volume data may be improved with greater grayscale value variations with regard to a medical diagnosis.

The present embodiments take into account that information about the area surrounding a region under investigation or "region of interest" (ROI) may be important for the assessment of the region. For example, in the course of breast examinations it is also of significance how the soft tissue in proximity to calcifications appears. In one embodiment, a slice region is specified in accordance with slice information within the considered volume data, and the slice region is visualized differently from its environment. With the different rendering, properties of the slice region are visualized (e.g., the complete suppression of the visualization of the slice region is not included). The slice region may be defined by a spherical, v-shaped or flat slice. The term "slice" may be understood in this context as being that an arbitrary (e.g., three-dimensional) sub-volume of an examined object is selected therewith. The sub-volume encompasses a subset of the volume data. The slice information required for specifying the slice may be furnished manually (e.g., using an input device such as a mouse or keyboard) or automatically. An automatic specification may be provided in accordance with object properties (e.g., anatomical characteristics). Alternatively, according to one embodiment, a whole sequence of slices may be generated automatically and stored for purposes of the diagnosis. In order to visualize the slice region, a first mapping of a value range of the volume data is used for visualizing the slice region on a display or monitor. In one embodiment, the mapping is chosen such that structures of interest in the slice region are shown with maximum precision. This information is supplemented with information about the environment. The provision of the supplementary information is achieved in that for visualizing a second region bordering on the slice region, a different mapping is used for the visualization on the display or monitor. The second mapping may be chosen such that relevant environmental information is visualized (e.g., bordering soft tissue). The term "mapping" may be that a rule is applied to influence which values of the volume data will be visualized or highlighted in the visualization. For example, the mappings utilize transfer functions that suitably translate or encode the values of the volume dataset for a visualization. When transfer functions are used, a value range of interest may be selected from the volume data (e.g., through the assignment of opacity values) for visualization on a monitor. In one embodiment, a window level specification may be used using one or both mappings. The windows are shifted to a value range of interest (e.g., in the area of calcifications (possibly around 500 Hounsfield units) for the slice region and in the adipose and connective tissue range (close to 0 Hounsfield units) for the bordering region).

The slice region or the bordering region may be visualized using direct volume rendering (e.g., ray casting) or using a maximum intensity protection (MIP) method. The bordering region may be visualized both as a three-dimensional zone and as a two-dimensional border region of the slice region using multiplanar reconstruction. In the case of multiplanar reconstruction, the representation is adapted by a mapping for the visualization of the two-dimensional surfaces so that relevant environmental information (e.g., adipose tissue) is shown. An arbitrary combination of the aforementioned methods may be used for the slice region and the bordering region.

The visualized volume data or grayscale values may have been obtained by measurements and, where applicable, by reconstruction. Medical imaging modalities may have been used for this (e.g., nuclear magnetic resonance tomography, computed tomography, X-ray machine, ultrasound device). In a tomosynthesis dataset or other datasets, in which the resolution is lower in one direction (e.g., the Z-direction), a visualization with viewing direction normal or substantially normal (e.g., up to 10°) to the direction of lower resolution is used.

Finally, provision can be made to enable zooming within the relevant data, and techniques such as depth curing and cut outlining can be employed to achieve a better perception of depth.

In one embodiment, a device for adjusting the visualization of volume data of an object as an image is provided. The device includes a computing device (e.g., a processor) configured to perform the processes disclosed above and below. For example, the processor is configured to specify at least one slice region in accordance with slice information within the volume data, and use a first mapping of a value range of the volume data for visualizing the at least one slice region on a display. The processor is also configured to use a second mapping different from the first mapping for visualizing a region bordering on the at least one slice region on the display.

In another embodiment, a non-transitory computer-readable medium that stores instruction executable by one or more processors to adjust the visualization of value data of an object as an image is provided. The instructions includes, for example, specifying at least one slice region in accordance with slice information within the volume data, and using a first mapping of a value range of the volume data for visualizing the at least one slice region on a display. The instructions also include using a second mapping different from the first mapping for visualizing a region bordering on the at least one slice region on the display.

BRIEF DESCRIPTION OF THE DRAWINGS

FIGS. 4a to 8 show exemplary breast images visualized by one embodiment of a method for adjusting the visualization of volume data of an object as an image.

DETAILED DESCRIPTION OF THE DRAWINGS

Figure 1:
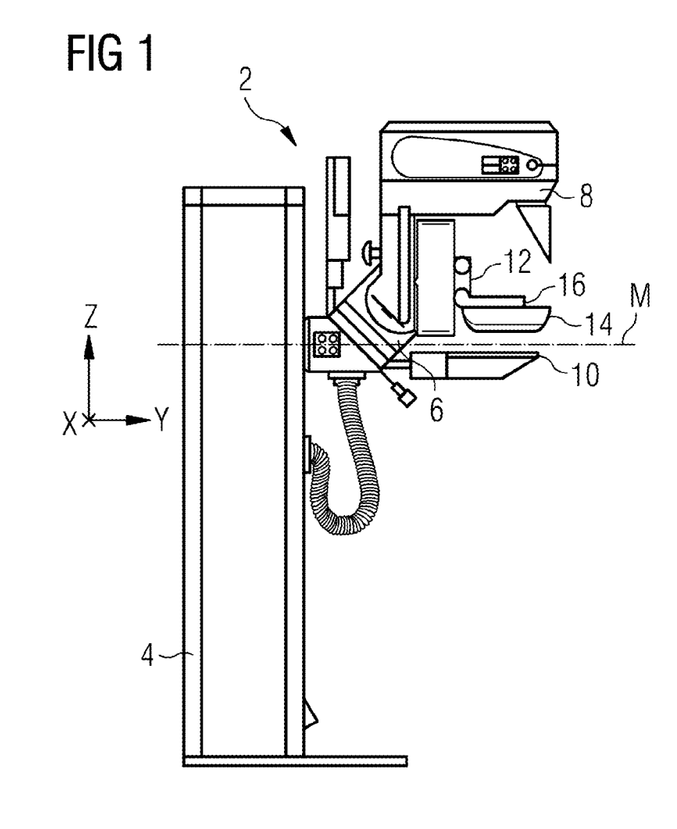
FIG. 1 shows a side view of one embodiment of a mammography device.
Figure 2:
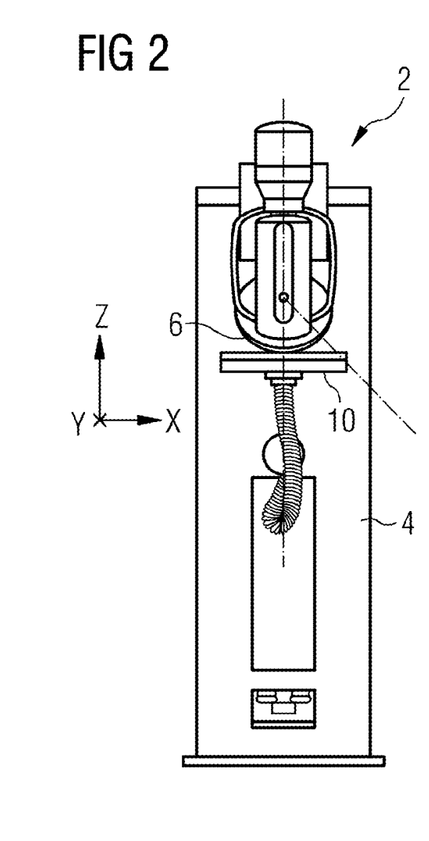
FIG. 2 shows a front view of one embodiment of the mammography device according to FIG. 1.

FIGS. 1 and 2 show a side view and a front view, respectively, of a mammography device 2. The mammography device 2 has a base body embodied as a stand 4 and, projecting out from the stand 4, an angled device arm 6. An irradiation unit 8 embodied as an X-ray emitter is arranged at a free end of the angled device arm 6. Also mounted on the device arm 6 are an object table 10 and a compression unit 12. The compression unit 12 includes a compression element 14 that is arranged relative to the object table 10 and is displaceable along a vertical Z-direction. The compression unit 12 also includes a support 16 for the compression element 14. In this arrangement, a type of lift guide is provided in the compression unit 12 for the purpose of moving the support 16 together with the compression element 14. Additionally, arranged in a lower section of the object table 10 is a detector 18 (cf. FIG. 3) that in the present exemplary embodiment is a digital detector.

Figure 3:
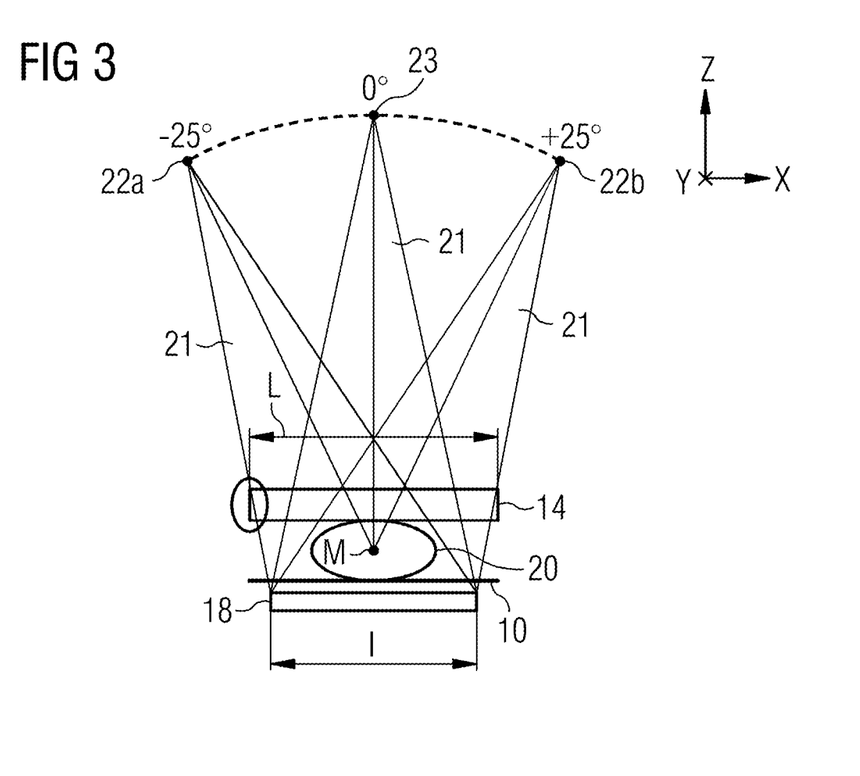
FIG. 3 shows two exemplary deflection positions during the irradiation using a mammography device in the case of tomosynthesis.

The mammography device 2 is provided, for example, for tomosynthesis examinations, in which the radiation unit 8 is moved through an angular range about a central axis M running parallel to the Y-direction, as shown in FIG. 3. In the process, a plurality of projections is obtained of the object 20 to be examined. The object 20 to be examined is held in a fixed position between the object table 10 and the compression element 4. As the images are recorded from the different angular positions, an X-ray beam 21 with a conical or fan-like cross-section passes through the compression element 14, the object 20 to be examined and the object table 10 and strikes the detector 18. The detector 18 is, for example, dimensioned such that the images may be recorded in an angular range between two deflection positions 22a, 22b at corresponding deflection angles of −25° or +25°. The deflection positions 22a, 22b are arranged in the X-Z plane on both sides of a zero position 23, at which the X-ray beam 21 is vertically incident on the detector 18. In the present exemplary embodiment, the planar detector 18 has, for example, a size of 24×30 cm.

Twenty-five projections are taken during the traversing of the trajectory from point 22a to point 22b. The examined object 20 is reconstructed from the recorded projections.

The reconstructed object may be present in the form of density values given at voxels or points in space. The density values constitute a metric for the respective density. In order to visualize object properties, pixel values are generated from the grayscale values for the visualization on a monitor.

Figure 4A:
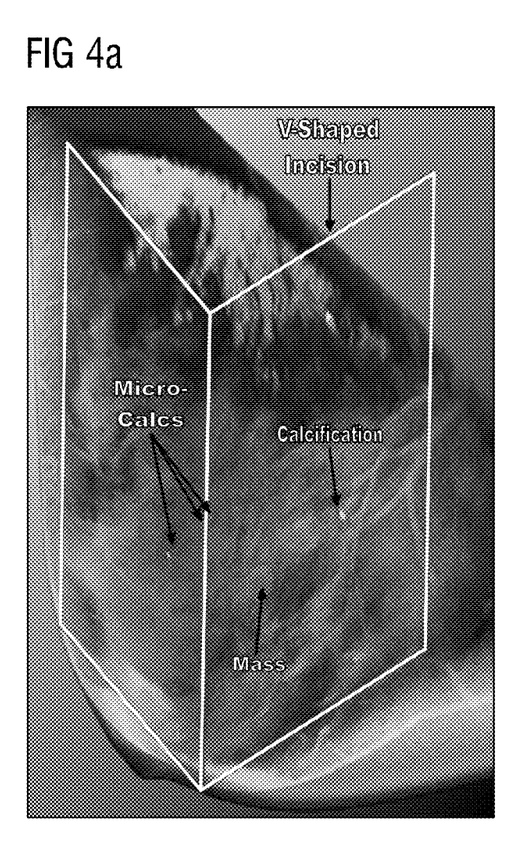
Figure 4B:
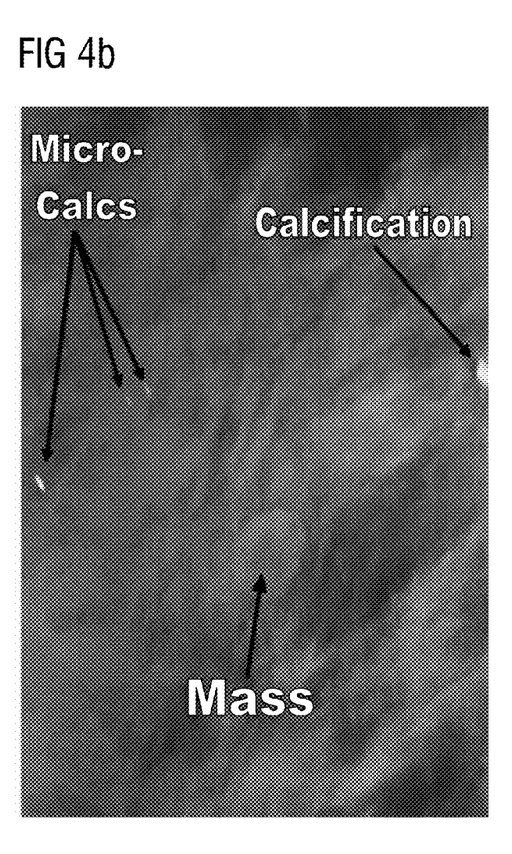

FIG. 4a shows a v-shaped slice (e.g., V-shaped incision) during a breast examination. Microcalcifications (e.g., Micro-Calcs), a larger calcification (e.g., Calcification) and a compressed tissue region (e.g., Mass) are shown. In FIG. 4b, the relevant parts are shown magnified or in a zoomed view.

Figure 5A:
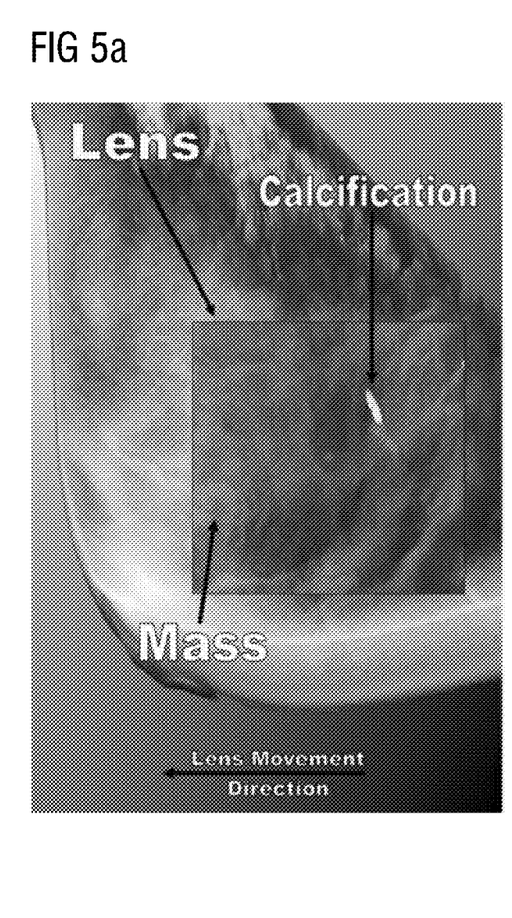
Figure 5B:
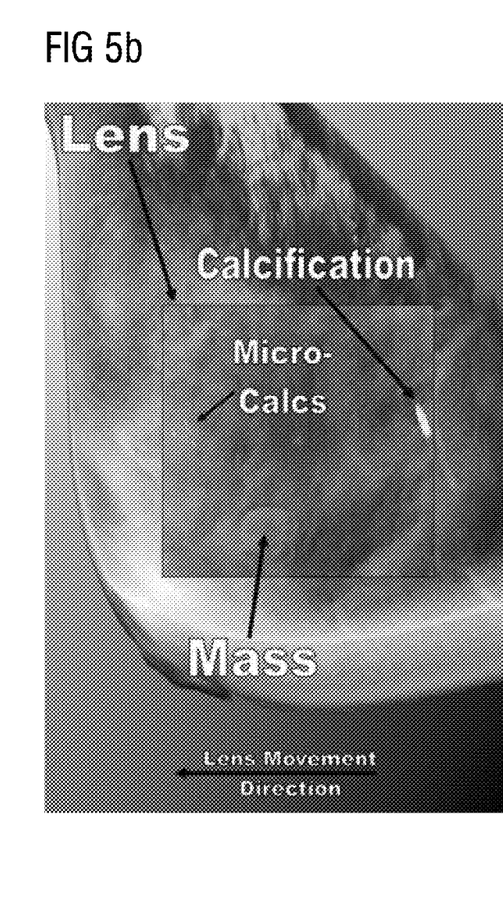

FIGS. 5a and 5b show two images of an automatically generated sequence of images. The magnified section (e.g., Lens) travels from right to left in the images. FIG. 5a shows a calcification (e.g., Calcification) and a compressed tissue region (e.g., Mass), which in FIG. 5b, have traveled to the right in the magnified section. Microcalcifications (e.g., Micro-Calcs) are also shown on the left-hand side in FIG. 5b. Thus, the entire object (e.g., breast) being examined may be scanned using an image sequence with moving section or lens.

Figure 6:
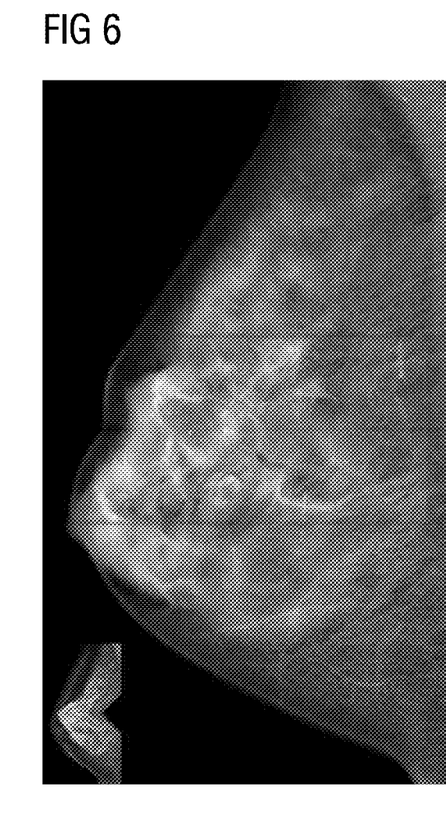
Figure 7:
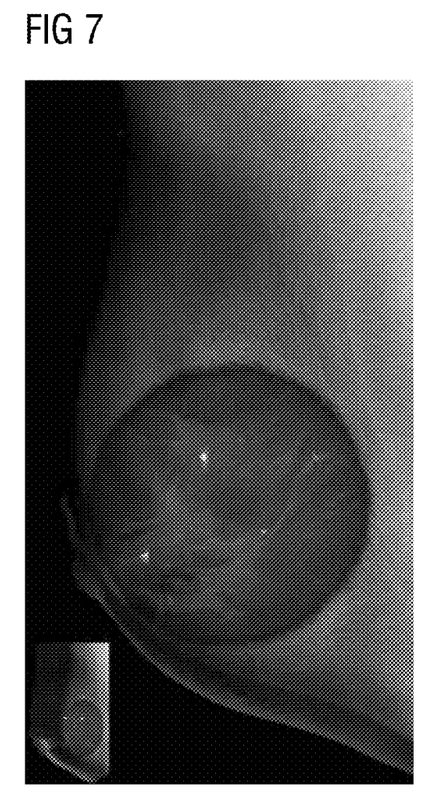

FIG. 6 shows a further image with a v-shaped slice, and FIG. 7 uses a spherical or ball-shaped slice. At bottom left in each case, the corresponding image is shown minimized and slightly rotated in order to convey a better impression of space to the viewer.

Figure 8:
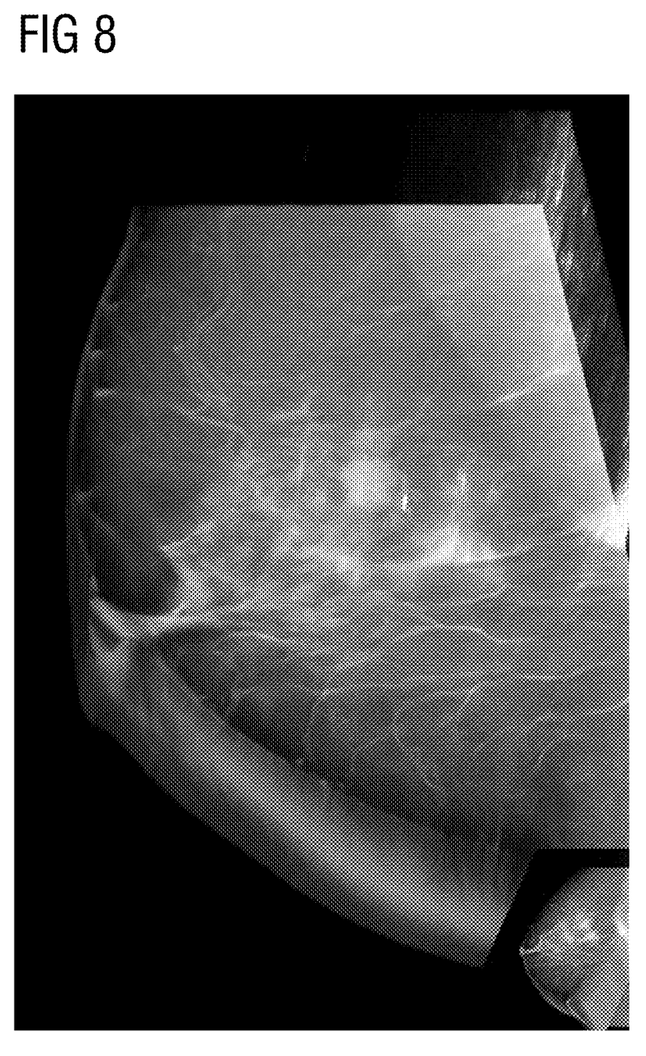

FIG. 8 shows by way of example a planar slice with a slightly rotated, minimized image at bottom right.

The data of the mammography dataset acquired during the tomosynthesis may represent the compressed breast. According to the present embodiments, a three-dimensional slice through the tissue (e.g., substantially adipose and connective tissue) is performed. The slice may have any shape; examples of spherical, v-shaped and planar slices are shown in the figures. The volume data outside the slice region may be visualized, for example, using direct volume rendering (e.g., ray casting) and suitable transfer functions or window definitions used for visualizing the tissue. Alternatively, the border zone of the slice region may be visualized using oblique MPRs. Within the slice region, the volume is visualized using MIP or direct volume rendering. In this case, for example, multidimensional transfer functions are used. With an appropriate window or window level specification or appropriately chosen transfer functions, calcifications in the slice region may be effectively visualized. In other words, if the slice is performed through the volume data, the calcifications appear. The calcifications are excised from the soft tissue. The calcifications are surrounded in the zone outside the slice region by the soft tissue, which is visualized. Thus, a user may identify how the calcifications are embedded in the soft tissue.

While the v-shaped slice region may be moved along the y-axis of the volume data (e.g., automatically or by user action), the planar slice region is moved along the x-axis of the dataset. In the case of an automatic movement of the slice region, the corresponding sequence of images may be stored in digital imaging and communications in medicine (DICOM) files (e.g., standard for medical images) for a subsequent diagnosis and viewed later using a workstation (e.g., part of a picture archiving and communication system (PACS)). This has the advantage that there is no increase in computing or resource requirements when reviewing the images, as is the case with actual volume rendering. In the case of slice regions under the control of the user, the images may be generated simultaneously (e.g., "on the fly"), or the rendering may be performed, for example, by using a high-performance graphic processing unit (GPU). In this case, the user is able to specify the slice region using a mouse (e.g., the v-shaped slice region travels along the data in accordance with the position of the mouse on the display). With a spherical slice region, this may be generated, for example, using a section of a ray with the mouse position within the volume dataset. In this case, as shown in FIG. 5, a zooming lens may be used. The window level adjustment inside and outside the slice region may be varied independently (e.g., the MIP visualization may be changed inside the slice region without this having an effect on the volume rendering outside the slice region). Parameters such as, for example, an incision radius or an aperture angle for the V may either be chosen automatically or set by the user. Owing to the lower Z-axis resolution of the data in tomosynthesis, the main viewing direction for the rendering of volume data may be orthogonal or almost orthogonal to the z-axis of the data in order to benefit from the higher resolution in the x- and y-direction. For orientation purposes and in order to give the user an overview of the slice region, an additional icon view (e.g., minimized visualization) may be displayed in a corner of the main image. The additional image shows the same image as the main image (e.g., with a slight variation in terms of orientation and zoom level). For example, this icon view may show the same rendering as the main view, though may be slightly zoomed out in comparison and represent a somewhat more lateral orientation in order to evoke a three-dimensional impression in the incision movement (cf. FIG. 8).

Techniques such as depth cueing and cut outlining may be employed in addition in order to improve depth perception and increase viewer concentration. Depth cueing improves depth perception by rendering tissue darker with increasing distance of the data from a virtual camera position. In cut outlining, a frame is generated around the slice region in order to increase the viewer's concentration level.

Figure 9:
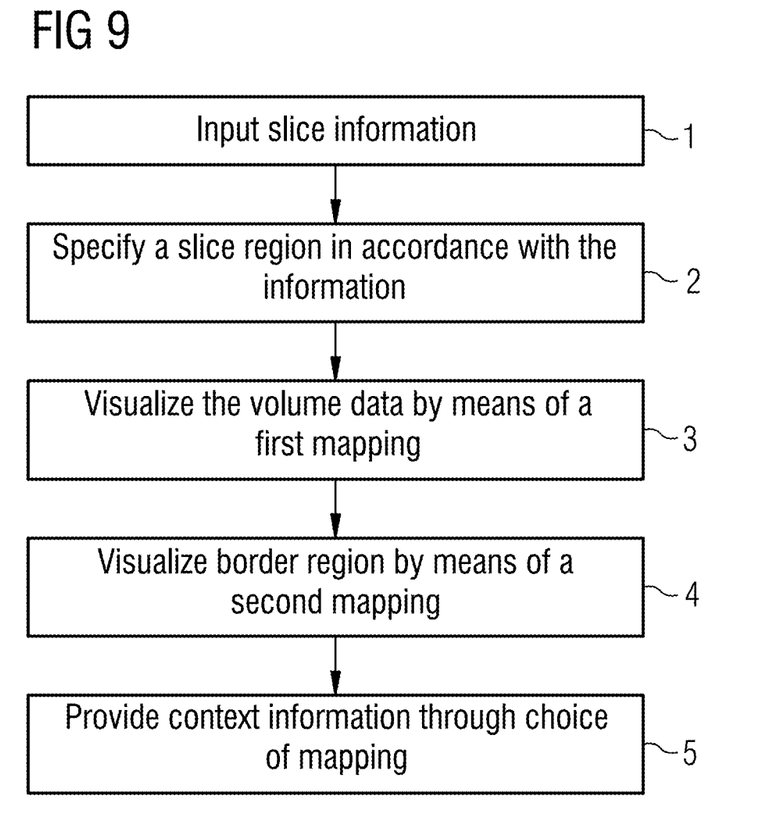
FIG. 9 shows a flowchart of one embodiment of a method for adjusting the visualization of volume data of an object as an image.

FIG. 9 shows a flowchart with basic elements of a method according to the present embodiments. Slice information is input in a first act. A slice region is specified (act 2) by the slice information. A first mapping is applied for visualizing the slice region (act 3). An environment or border zone of the slice region is visualized by a second mapping (act 4). The first mapping and the second mapping (e.g., mappings) are chosen so that relevant information (e.g., context information) relating to the embedding of the slice region in the volume is obtained (act 5).

The above description of embodiment elements is purely illustrative and is not to be interpreted as limiting the subject matter, for which protection is sought. Different or further embodiment elements and embodiment variants may be derived directly by those of ordinary skill in the art.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for adjusting a visualization of volume data of an object as an image with regard to diagnostically relevant medical information relating to an environment of a region under investigation, the method comprising:
specifying at least one slice region in accordance with slice information within the volume data;
using a first mapping of a value range of the volume data for visualizing the at least one slice region on a display; and
using a second mapping different from the first mapping for visualizing a region bordering on the at least one slice region on the display,
wherein the first mapping, or the first mapping and the second mapping use at least one transfer function or a window level specification,
wherein the at least one transfer function, the window level specification, or the at least one transfer function and the window level specification of the first mapping are selected in accordance with a visualization of calcifications, adipose, or connective tissue,
wherein the first mapping is selected in accordance with the visualization of calcifications, and
wherein the second mapping is selected in accordance with the visualization of adipose or connective tissue.

2. The method as claimed in claim 1, wherein the at least one slice region, the bordering region, or the at least one slice region and the bordering region are visualized using volume rendering.

3. The method as claimed in claim 1, wherein the at least one slice region, the bordering region, or the at least one slice region and the bordering region are visualized using an MIP method.

4. The method as claimed in claim 1, wherein a bordering zone comprises a border region of the at least one slice region, and
wherein the border region is visualized using multiplanar reconstruction.

5. The method as claimed in claim 1, further comprising acquiring the volume data using tomosynthesis.

6. The method as claimed in claim 1, further comprising specifying the at least one slice region according to at least one spherical, v-shaped or planar slice.

7. The method as claimed in claim 1, further comprising:
providing a direction, in which the volume data is present at a lower resolution in comparison with directions normal to the direction; and
performing a visualization with a viewing direction substantially normal to the lower-resolution direction.

8. The method as claimed in claim 1, further comprising:
automatically specifying the slice information automatically in accordance with object properties or determining the slice information during a presetting process; and
automatically correlating at least one slice with the slice information.

9. The method as claimed in claim 8, further comprising generating and storing a sequence of images with slices differing from one another.

10. The method as claimed in claim 1, wherein the slice information is inputtable by a user with the aid of an input device.

11. The method as claimed in claim 10, further comprising generating a recomputation of the image in response to the input of the slice information by the user.

12. A device for adjusting a visualization of volume data of an object as an image with regard to diagnostically relevant medical information relating to an environment of a region under investigation, the device comprising:
a display; and
a processor in communication with the display and configured to:
specify at least one slice region in accordance with slice information within the volume data;
use a first mapping of a value range of the volume data for visualizing the at least one slice region on the display; and
use a second mapping different from the first mapping for visualizing a region bordering on the at least one slice region on the display,
wherein the first mapping, or the first mapping and the second mapping use at least one transfer function or a window level specification,
wherein the at least one transfer function, the window level specification, or the at least one transfer function and the window level specification of the first mapping are selected in accordance with a visualization of calcifications, adipose, or connective tissue,
wherein the first mapping is selected in accordance with the visualization of calcifications, and
wherein the second mapping is selected in accordance with the visualization of adipose or connective tissue.

13. The device as claimed in claim 12, further comprising a unit operable to zoom in on a visualized image section.

14. The device as claimed in claim 12, further comprising a unit operable to improve the depth perception of a visualized image section.

15. In a non-transitory computer-readable medium that stores instructions executable by one or more processors to adjust a visualization of volume data of an object as an image with regard to diagnostically relevant medical information relating to an environment of a region under investigation, the instructions comprising:
specifying at least one slice region in accordance with slice information within the volume data;
using a first mapping of a value range of the volume data for visualizing the at least one slice region on a display; and
using a second mapping different from the first mapping for visualizing a region bordering on the at least one slice region on the display,
wherein the first mapping, or the first mapping and the second mapping use at least one transfer function or a window level specification,
wherein the at least one transfer function, the window level specification, or the at least one transfer function and the window level specification of the first mapping are selected in accordance with a visualization of calcifications, adipose, or connective tissue,
wherein the first mapping is selected in accordance with the visualization of calcifications, and
wherein the second mapping is selected in accordance with the visualization of adipose or connective tissue.

* * * * *